(12) United States Patent
Caduff et al.

(10) Patent No.: US 9,155,505 B2
(45) Date of Patent: Oct. 13, 2015

(54) WEARABLE SENSOR DEVICE

(75) Inventors: Andreas Caduff, Schmerikon (CH); Hans-Joachim Krebs, Lachen (CH); Gianlucca Stalder, Wildberg (CH); Mark Stuart Talary, Zürich (CH)

(73) Assignee: BIOVOTION AG, Zurich (CH)

( * ) Notice: Subject to any disclaimer, the term of this patent is extended or adjusted under 35 U.S.C. 154(b) by 375 days.

(21) Appl. No.: 13/577,025

(22) PCT Filed: Feb. 5, 2010

(86) PCT No.: PCT/CH2010/000034
§ 371 (c)(1),
(2), (4) Date: Oct. 10, 2012

(87) PCT Pub. No.: WO2011/094875
PCT Pub. Date: Aug. 11, 2011

(65) Prior Publication Data
US 2013/0211204 A1    Aug. 15, 2013

(51) Int. Cl.
*A44C 5/00*    (2006.01)
*A45F 5/00*    (2006.01)
(Continued)

(52) U.S. Cl.
CPC .............. *A61B 5/6831* (2013.01); *A44C 5/00* (2013.01); *A45F 3/14* (2013.01); *A45F 5/00* (2013.01); *A61B 5/01* (2013.01); *A61B 5/053* (2013.01); *A61B 5/14532* (2013.01); *A61B 5/6843* (2013.01); *A61B 8/06* (2013.01); *A61B 5/0059* (2013.01); *A61B 5/02055* (2013.01); *A61B 5/0261* (2013.01); *A61B 5/0265* (2013.01); *A61B 5/02438* (2013.01); *A61B 5/1455* (2013.01); *A61B 5/6824* (2013.01); *A61B 5/7207* (2013.01)

(58) Field of Classification Search
CPC ........ A45F 5/00; A61B 5/681; A61B 5/6831; A61B 5/1455; A61B 5/0265; A61B 8/06
USPC ......... 224/222, 219, 164, 167, 168, 171, 180; 128/644
See application file for complete search history.

(56) References Cited

U.S. PATENT DOCUMENTS 1,898,402 A * 2/1933 Smith .............................. 59/80
5,243,992 A * 9/1993 Eckerle et al. ................ 600/503
(Continued)

FOREIGN PATENT DOCUMENTS

WO    02/065901 A2    8/2002
WO    2009/000024 A1    12/2008

OTHER PUBLICATIONS

International Preliminary Report on Patentability and International Search Report dated Sep. 29, 2010 for Application No. PCT/CH2010/000034.
(Continued)

*Primary Examiner* — Justin Larson
*Assistant Examiner* — Lester L Vanterpool
(74) *Attorney, Agent, or Firm* — Ladas & Parry LLP (57) ABSTRACT

A sensor device comprises a sensor (1) to be held against the wearer's skin. The sensor (1) is arranged on one side of a housing (2), and the housing is connected to a band (5) for mounting it to a body part, such as an arm or leg. Various stopper devices (10, 14, 20) are arranged on the side of the housing (2) and the band (5) that face the skin. The stopper devices improve static friction, thereby holding the housing (2) in place.

13 Claims, 6 Drawing Sheets

(51) Int. Cl.

| | | |
|---|---|---|
| *A45F 3/14* | (2006.01) | |
| *A61B 5/00* | (2006.01) | |
| *A61B 5/01* | (2006.01) | |
| *A61B 5/053* | (2006.01) | |
| *A61B 5/145* | (2006.01) | |
| *A61B 8/06* | (2006.01) | |
| *A61B 5/024* | (2006.01) | |
| *A61B 5/0205* | (2006.01) | |
| *A61B 5/026* | (2006.01) | |
| *A61B 5/0265* | (2006.01) | |
| *A61B 5/1455* | (2006.01) | |

(56) References Cited

U.S. PATENT DOCUMENTS

| | | | | |
|---|---|---|---|---|
| 5,471,983 | A * | 12/1995 | Magnus | 600/390 |
| 5,738,104 | A * | 4/1998 | Lo et al. | 600/521 |
| 5,769,290 | A * | 6/1998 | Pestana | 224/178 |
| 5,795,300 | A * | 8/1998 | Bryars | 600/500 |
| 5,901,373 | A * | 5/1999 | Dicker | 2/69 |
| 6,238,354 | B1 * | 5/2001 | Alvarez | 600/549 |
| 6,529,754 | B2 * | 3/2003 | Kondo | 600/344 |
| 6,928,317 | B2 * | 8/2005 | Chen | 600/509 |
| 7,190,986 | B1 * | 3/2007 | Hannula et al. | 600/344 |
| 7,591,581 | B2 * | 9/2009 | Lovegrove et al. | 368/281 |
| 7,625,625 | B2 * | 12/2009 | Rios et al. | 428/141 |
| 2002/0151775 | A1 * | 10/2002 | Kondo | 600/344 |
| 2004/0065158 | A1 | 4/2004 | Schrepfer et al. | |
| 2005/0275416 | A1 | 12/2005 | Hervieux et al. | |
| 2007/0015980 | A1 | 1/2007 | Numada et al. | |
| 2007/0064542 | A1 | 3/2007 | Fukushima | |
| 2007/0282180 | A1 | 12/2007 | Caduff et al. | |
| 2008/0249393 | A1 | 10/2008 | Finarov et al. | |
| 2009/0312615 | A1 | 12/2009 | Caduff et al. | |
| 2010/0240977 | A1 | 9/2010 | Caduff | |
| 2010/0298680 | A1 | 11/2010 | Talary et al. | |
| 2011/0160554 | A1 | 6/2011 | Magej et al. | |
| 2012/0095307 | A1 | 4/2012 | Caduff et al. | |

OTHER PUBLICATIONS

Zakharov, P., et al., "A wearable diffuse reflectance sensor for continuous monitoring of cutaneuos blood content", Physics in Medicine and Biology 54, (2009), pp. 5301-5320.

* cited by examiner

WEARABLE SENSOR DEVICE

RELATED APPLICATION INFORMATION

This application is a 371 of International Application PCT/CH2010/000034 filed 5 Feb. 2010 entitled "WEARABLE SENSOR DEVICE", which was published in the English language on 11 Aug. 2011, with International Publication Number WO 2011/094875 A1, the content of which is incorporated herein by reference.

TECHNICAL FIELD

The invention relates to a wearable sensor device for measuring a physiological parameter of a wearer. The invention also relates to a method for operating the device. In particular, it relates to a wearable sensor device comprising a housing and a band, wherein the housing has a sensor that is to be held against the wearer's skin, and the band is attached to the housing and is to be wound around a body part, such as an arm or leg, of the wearer.

BACKGROUND ART

WO 2009/086643 describes a wearable sensor device for determining a physiological parameter of its wearer, such as glucose level. It comprises a housing with a set of electrodes arranged at its bottom side. A wristband is attached to the housing for being wound at least once around an arm or leg of the wearer and for attaching the housing with its electrodes facing the wearer's skin.

A similar device is disclosed in WO 2007/053963, which, in addition to electrodes, comprises optical sensors and temperature sensors, also to be worn against its wearer's skin. Again, the housing of the device is held by means of a wristband against a body part of the wearer. The device can e.g. be used to measure glucose level, blood perfusion, or surface water content.

DISCLOSURE OF THE INVENTION

The problem to be solved by the present invention is to provide a sensor of this type with improved signal accuracy.

This problem is solved by the device according to claim 1. Accordingly, the device comprises a housing having at least one sensor. The sensor is arranged on a "first side" of the housing, namely on the side that is to be applied against the wearer's skin. The device further comprises a flexible band connected to the housing. The flexible band is structured in length and flexibility to be wound around a body part of the wearer, such as an arm or leg, advantageously an upper arm, and its purpose is to hold the housing against the wearer's skin. The band has a first side (inner side) that is facing the wearer's skin when the device is worn. In addition, the sensor device is equipped with at least one stopper device arranged over a surface of the first side of the housing or over a surface of the first side of the band. The stopper device has a higher coefficient of static friction (with respect to human skin) than said surface of the housing or the band.

Hence, the stopper device improves static friction of the sensor device on the wearer's skin, thereby making it more difficult to move the sensor with respect to the skin. Since such a movement leads to signal artifacts, the stopper device helps to render the sensor device more accurate.

In an advantageous embodiment, the stopper device comprises a flexible strip having a first end attacked to the housing. The stopper device extends along part of the first side (inner side) of the band. The second end of the stopper device strip, i.e. the end opposite the first end, is movable with respect to the band. In other words, the strip is (at one end) connected to the housing in a fixed manner, but it can move, over at least part of its length, with respect to the band. As it is arranged along the first side of the band, i.e. the side that faces the user's skin, the band holds the strip against the body during normal operation, such that a high static friction develops between the strip and the body. Since the strip is connected to the housing, it can hold the housing in place. However, if the band moves in its longitudinal direction, e.g. due to muscle movement, such movement is not or only weakly transferred to the strip.

To improve the mechanical isolation that is provided by the strip between band motion and skin, the strip has advantageously a higher coefficient of static friction with respect to the skin than with respect to the first surface (inner surface) of the band.

In another advantageous embodiment, the sensor device comprises at least one stopper device affixed to the first side of the housing. Such a stopper device helps to directly hold the housing stationary with respect to the skin.

In yet another advantageous embodiment, the sensor device comprises at least one stopper device affixed to the band. This type of stopper device helps to improve static friction between the band and the wearer's skin.

In an advantageous aspect of the invention, the above device is operated by affixing it to an upper arm of the wearer.

The various types of stopper devices can be combined in a single sensor device.

BRIEF DESCRIPTION OF THE DRAWINGS

The invention will be better understood and objects other than those set forth above will become apparent when consideration is given to the following detailed description thereof. Such description makes reference to the annexed drawings, wherein.

MODES FOR CARRYING OUT THE INVENTION

Figure 1:
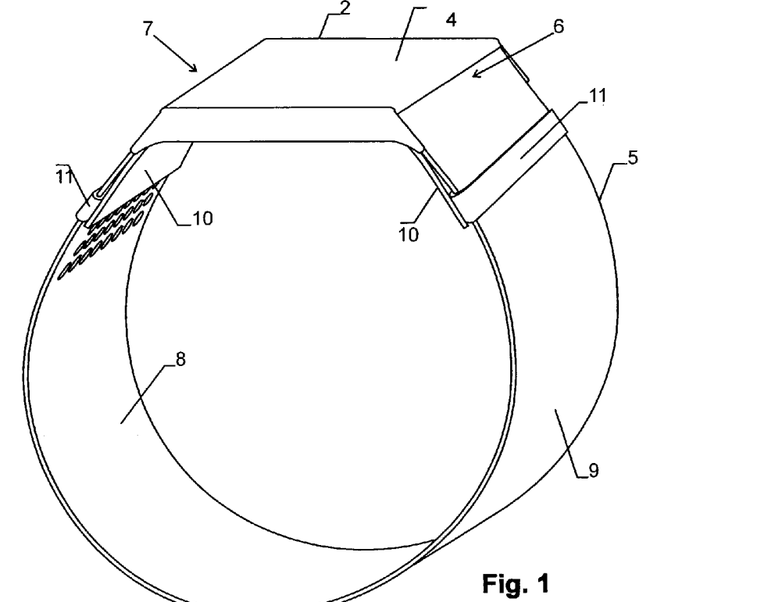
FIG. 1 shows a first view of the of an embodiment of the sensor device.
Figure 2:
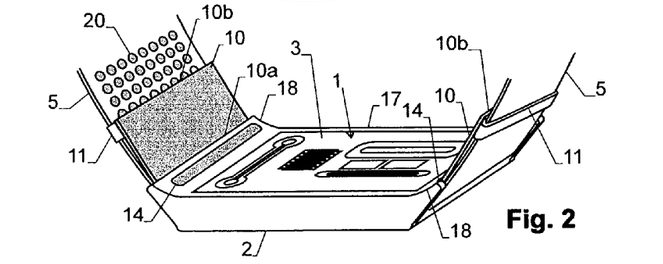
FIG. 2 shows a second view of the device of FIG. 1.
Figure 3:
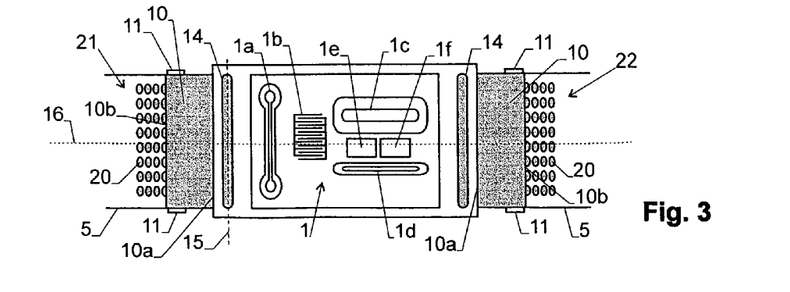
FIG. 3 shows a third view of the device as seen perpendicularly to the first side (bottom side) of the housing.

An advantageous embodiment of the sensor device is shown in FIGS. 1-3. The sensor device comprises a sensor 1 for measuring a physiological parameter of the wearer. Sensor 1 is adapted to operate when being applied to the wearer's skin. There are various types of such sensors known to the skilled person, for example:

Glucose level sensors as e.g. described in WO 2009/086643 or WO 2007/053963. This type of sensor e.g. measures the response of the tissue to an applied electric field, optionally in combination with optical reflection measurements and temperature measurements. The sensor device shown in the figures schematically depicts such a sensor 1 with electrodes 1a, 1b, 1c, 1d and optical reflection sensors 1e, 1f (FIG. 3). WO 2009/086643 and WO 2007/053963 are incorporated by reference herein.

Blood perfusion sensors or pulse rate sensors. Such sensors may use optical and/or electrical measurements for determining the blood concentration and/or pulse rate. An example for such a sensor device is described in US 2009/0099462.

Other types of sensor devices may e.g. include devices adapted to carry out temperature measurements for determining body temperature, ultrasonic measurements for determining blood flow properties, and others, or they may be based on any combination of such sensor technologies.

Most advantageously, though, the present invention is used for sensors having electrodes for measuring a response of the tissue to an applied electric field since such sensors are sensitive to motions of the electrode device with respect to the skin.

The sensor device of FIGS. 1-3 further comprises a housing 2, e.g. of plastics and/or metal, which typically contains control circuitry and a power supply for the sensor 1. Sensor 1 is arranged on a first side 3 of the housing, which is the side that, during operation of the device, is facing the wearer's skin. An opposite, second side 4 of housing 2 is, in operation, facing away from the wearer's skin.

An elongate, flexible band 5 is attached to housing 2 and is adapted to be wound around a body part of the wearer for holding first side 3 of housing 2 against the wearer's skin. The length of band 5 may be fixed or variable, and is adapted to the length of the body part on which the device is to be worn on. Typically, the device is worn on an arm or a leg, advantageously on the upper arm. However, the device may e.g. also be worn around the chest.

Figure 4:
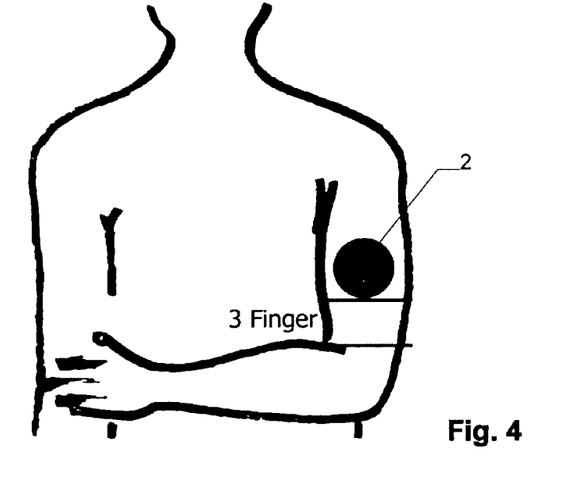
FIG. 4 illustrates a suitable position of the housing on the arm of the wearer.

In a particularly advantageous embodiment of the invention, housing 2 is affixed antero-laterally to the upper arm, on the middle of the musculus biceps brachii, in particular three fingers above the fossa anconal. This is illustrated in FIG. 4. At this location, the muscle layer is thin and movements have therefore reduced tendency to affect the measurement (for experimental results see below).

When the arm is bent 90° and is held in front of the body, the device should sit on top of the arm. If the person wearing the sensor has a strong bicep, the sensor should preferably be placed a bit (e.g. 5 mm-1 cm) more to the outside (away from the chest). If the person has a strong tricep, the sensor should be placed more inside (e.g. 5 mm-1 cm) than normal (towards the chest). If the M. deltoideus (Deltamuskel) is very strong, care should be taken to not place the sensor too high.

The ends of band 5 are fixedly or releasably attached to opposite sides 6, 7 of housing 2. In operation, band 5 is slightly distended and exerts a pulling force on housing 2, which provides a force for pulling the device against the wearer's skin.

Band 5 can be moisture permeable in order to allow skin moisture to escape. Advantageously, a first side 8 of band 5, namely the side that faces the wearer's skin, is of a hydrophobic material, while a second, opposite side 9 of band 5 is of a hydrophilic material. This design expedites the carrying off of moisture from the skin.

Band 5 can be of a textile material. An example of a material having the hydrophilic and hydrophobic properties mentioned above is Eschler e3 protection fabric, Art. Nr. 63645 by Eschler Textil GmbH, Balingen (DE), from which a band having a width of 4.5 cm and a length between 16 and 22 cm, advantageously 18.5 cm, is formed.

Band 5 should be elastic in order to allow a convenient and reliable adjustment of the force provided for pulling housing 2 against the body part. If band 5 is not sufficiently elastic, it will be difficult to adjust and maintain the correct force of attachment, and if the band is too elastic, the band will not be flexible to absorbing movements of the body without disturbing the contact of the skin.

Advantageously, the elasticity of band 5 is between 0.20 and 0.32 N/%, in particular 0.26 N/%, with said elasticity expressing the change of longitudinal force under 1% change of length.

The length of the band is selected thus that, in normal wearing position, it is extended by 20% and generates, parallel to the band's longitudinal axis, a force of 5 N.

As mentioned above, the sensor device can be equipped with one or more stopper devices. Such stopper devices are marked with a grey pattern in FIGS. 2 and 3. Each stopper device is arranged on first surface (inner surface) 3 of housing 2 and/or on first surface (inner surface) 8 of band 5 and has a higher coefficient of static friction (with respect to skin) than the surface 3, 8 it is arranged on.

The term "coefficient of static friction with respect to skin" is understood to be an average coefficient of static friction as observed when the surface in question is applied to a set of at least ten wearers under conditions comparable to the normal operation of the device.

To improve static friction, the stopper devices can be soft, i.e. softer than the surface they reside on, and/or elevated over that surface.

Advantageously, at least the surface of the stopper devices (or at least of some of them) is made of silicone.

The stopper devices, as well as any other parts of the sensor device coming into contact with the wearer's skin, should exhibit a low level of hypersensitisation of the skin.

The embodiment shown in FIGS. 1-3 has different types of stopper devices, which will be explained to in the following.

A first type of stopper device is formed by one or two flexible strips 10. Each flexible strip 10 has a first end 10a attached to the housing and a second, opposite, free end 10b. Between its ends 10a, 10b, strip 10 extends along part of the first side 8 of band 5. However, there is, at least over a substantial length of the strip, such that at least over 50% of its length or even all of its length, no direct, fixed connection between strip 10 and band 5, thus that the second end 10b of strip 10 is movable along band 5.

Optionally, a strap 11 is attached to strip 10, close to the second end 10b, and extends around band 5 for loosely holding strip 10 against the band.

As can be seen in FIGS. 2 and 3, the two strips 10 are arranged on opposite lateral sides 6, 7 of housing 2, with a first of the strips 10 being located at a first end of band 5 and a second one of the strips 10 being located at a second end of band 5, thus providing anchorage to both sides of housing 2.

The strip or strips 10 can be made of a plastics material having a high coefficient of static friction, at least on its side facing away from band 5, i.e. on its side facing the wearer's skin. Instead of using a plastics material, a textile material can be used, advantageously with an additional frictional coating or structure on the side facing the wearer's skin.

The strip or strips 10 should have a length of at least 1 cm, in particular between 2 and 4 cm.

The width of the strips 10 should be approximately equal to the width of band 5 in order to provide a maximum of usable friction surface.

An important advantage provided by using strips 10, as mentioned, lies in the fact that they do not follow a longitudinal distension of band 5 (e.g. in response to the wearer flexing his/her muscles in the body part) while always being pressed firmly against the user's skin, thereby anchoring housing 2 securely and without distorting the skin below them.

A second type of stopper device is formed by frictional structures 14 affixed to first side 3 of housing 2. Advantageously, at least a first and a second frictional structure 14 are arranged at opposite sides of sensor 1. Each frictional structure 14 is longitudinal with a longitudinal axis 15 extending transversally, in particular perpendicularly, with respect to a longitudinal axis 16 of band 5 (cf. FIG. 3), thus providing a long area of frictional interaction with the body part.

As can best be seen from FIG. 2, housing 2 forms, at its first side 3, a recess, which has a flat bottom 17 receiving sensor 1 and opposite side walls 18, which are inclined with respect to bottom 17, thus that a wide groove is provided for receiving the roughly cylindrical body part. The frictional structures or stopper devices 14 are advantageously arranged on the side walls 18, thus that they can engage the body part from lateral, opposing sides.

A third type of stopper device is affixed to first side 8 of band 5. Each third type of stopper device is advantageously formed by a nub 20, with said nubs 20 forming at least two arrays 21, 22. Using arrays of nubs 20 has the advantage that a high friction can be achieved over a large surface area while still leaving the band permeable between the nubs.

The nubs 20 are e.g. made from a silicone material, and they have diameters between 0.5 and 3 mm and a height between 0.1 and 1 mm.

The arrays of nubs 20 are advantageously arranged close to the ends of band 5, i.e. close to housing 2 in order to anchor the housing.

It must be noted that the three different types of stopper devices 10, 14 and 20 can be used alternatively or in combination. For example, in particular when providing the strips 10, the nubs 20 may also be dispensed with because the strips 10 may provide sufficient and better anchoring for housing 2.

EXPERIMENTS

Figure 6:
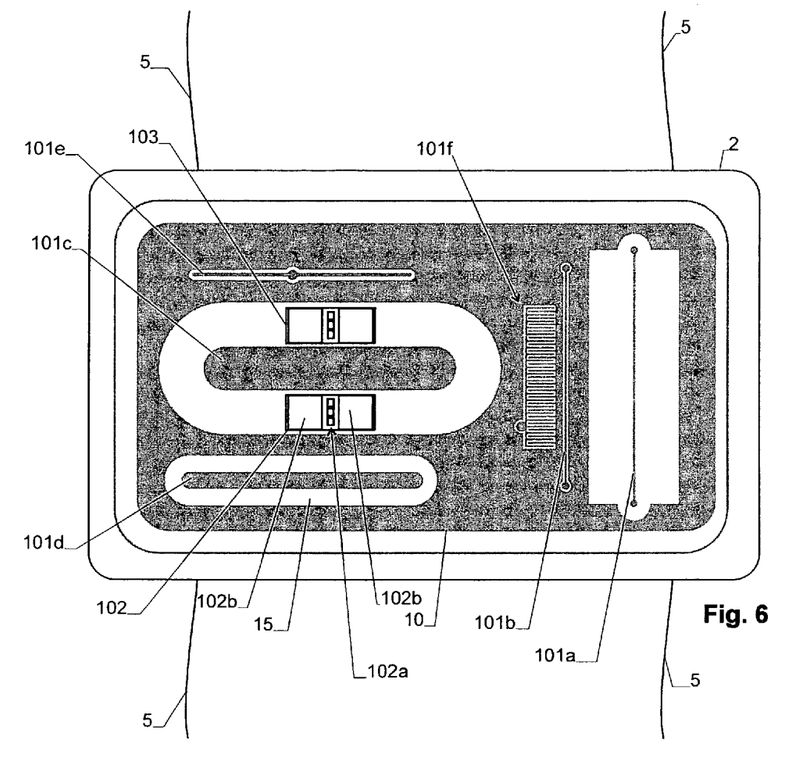
FIG. 6 shows a second embodiment of a device from its first side.

The device:

A series of experiments were carried out on a device designed to run impedance measurements in a series of frequency ranges. FIG. 6 shows the electrodes and other sensors of this device.

The device comprises two electrodes 101a, 101b designed as coplanar waveguides and adapted to perform measurements at frequencies of 1-10 GHz. Both consist of a strip-shaped inner electrode, which is connected to a signal source at one end and a signal detector at the opposite end. Each strip-shaped inner electrode is surrounded by a ground electrode. The gap between the inner electrode and the ground electrode is 4 mm and 0.15 mm, respectively. The electronics connected to the electrodes 101a, 101b measure the complex trans-mission factor $Z_{GHz}=U_{out}/U_{in}$, with $U_{out}$ and $U_{in}$ being the complex voltages at the output and the input of each coplanar waveguide.

WO 2009/152624 describes a method for measuring the factor $Z_{GHz}$ and is incorporated herein by reference.

The device further comprises three electrodes 101c, 101d, 101e adapted to perform measurements at a frequency of 0.1-100yyy MHz. Each electrode consists of an inner strip electrode surrounded by a ground electrode. The gap between the inner strip electrode and the ground electrode is 4 mm, 1.5 mm and 0.3 mm, respectively. Each inner strip electrode is connected to a signal at a single contact point. The electronics connected to the electrodes 101c, 101d, 101e measure a complex factor $Z_{MHz}$ proportional to the impedance between the signal electrode and the ground electrode.

The device also comprises an electrode 101f, which is an interdigitated electrode surrounded by a ground electrode and adapted to perform measurements at a frequency of 1-200 kHz. A signal from a signal generator is fed to a contact point in the center of electrode 101f, and a factor $Z_{kHz}$ proportional to the impedance between the signal electrode and the ground electrode is measured, as described in WO 2007/053963.

Further, the device comprises two optical sensors 102, 103, each comprising at least an infrared light source 102a operating in the visible and NIR spectral range and two light detectors 102b. Each optical sensor measures a signal proportional to the reflectance of the tissue for the light emitted by the light source.

Finally, the device comprises a temperature sensor in thermal contact with the ground electrode for measuring skin temperature.

Figure 5:
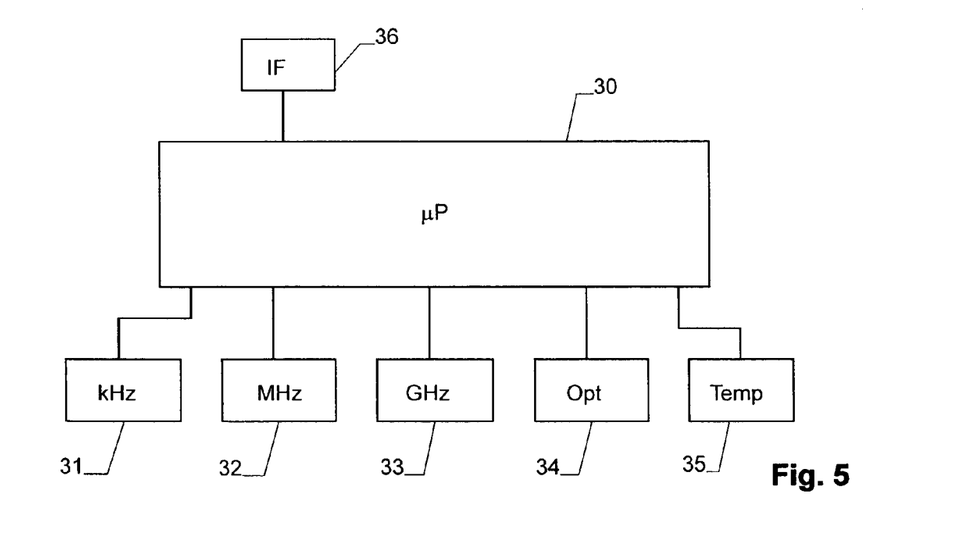
FIG. 5 is a block circuit diagram of a device.

FIG. 5 shows a block diagram of the device. As can be seen, the device comprises a control unit 30, e.g. a microprocessor with program and data memory as known to the skilled person, which controls the operation of the device. Control unit 30 is connected to various sensor units, in particular:

a) A low-frequency sensor unit 31 comprising a signal generator and signal detector at 1 kHz, which uses the interdigital electrodes 101f for its measurements.

b) A medium-frequency sensor unit 32 comprising a signal generator and signal detector at the frequency of 0.1-100 MHz, which uses the electrodes 101c, 101d, 101e for its measurements.

c) A high-frequency sensor unit 33 comprising a signal generator and signal detector at the frequency of 1-10 GHz, which uses the electrodes 101a, 101b for its measurements.

d) An optical detector unit 34 measuring optical reflection by means of the optical sensors 23a, 102, 103.

e) A temperature sensor unit 35 measuring the temperature of the surface of the tissue.

Measurement:

To determine the dependence of the signals measured by the various sensor units on different parameters, such as on the position of the device or the type of band 5, various experiments have been carried out. In each experiment, the signals from the sensor unit was recorded over a time period of up to 10 minutes at every 20 seconds. During the measurement the wearer performed specific movements according to an experimental protocol, while the sensor unit was placed at slightly different positions. The "noise" in each signal X was determined by first calculating a smoothed signal $X_f$ using a Butterworth lowpass filter, namely an infinite response filter having 4 a and 4 b coefficients. The transient response time of the filter was 4.7 minutes.

Then the power of the noise is defined in the logarithmic scale by means of the decimal logarithm of the variance of the high-frequency residual, i.e.

$$\log \text{NoisePower}=10 \cdot \log_{10}(\text{Var}(X-X_f))$$

with Var( ) being the variance. Then the signal power is defined as the decimal logarithm of the variance of filtered signal $X_f$:

$$\log \text{SignalPower}=10 \cdot \log_{10}(\text{Var}(X_f))$$

In this way, the signal-to-noise ratio can be found by subtracting the logarithm of noise power from the logarithm of signal power, i.e.

$$\text{SNR}=\log \text{SignalPower}-\log \text{NoisePower}$$

The SNR values for the following signals were measured:

The magnitude and the phase of the signal measured by low-frequency sensor 31 at 10 kHz. In the following figures, the corresponding values contain the string "kHz-ell-mag" in their name for the magnitude and "kHz-ell-phase" for the phase.

The magnitude and the phase of the signal measured by the medium-frequency sensor 32 at 30 MHz. In the following figures, the corresponding values contain the string "MHz-elX-mag" and "MHz-elX-phase" (for magnitude and phase), with X being 1 for electrode 101*c*, 2 for electrode 101*d*, 3 for electrode 101*e*.

The magnitude and the phase of the signal measured by the high-frequency sensor 33 at 2.05 GHz. In the following figures, the corresponding values contain the string "GHz-elX-mag" and "GHz-elX-phase" (for magnitude and phase), with X being 1 for electrode 101*a*, 2 for electrode 101*b*.

The SNR of the optical reflection measurements contain the string "Opt_en1" and "Opt-en2" in their name and were measured at 800 nm.

The SNR signal of the temperature sensor is denoted by Ted_skin_Temp.

Results:

a) Position Dependence

To determine the effects of the position of the device on the body, the device of FIGS. 5 and 6 was attached to the upper left arm of a wearer at various positions and the SNR of the various signals was measured in the manner described above.

Figure 7:
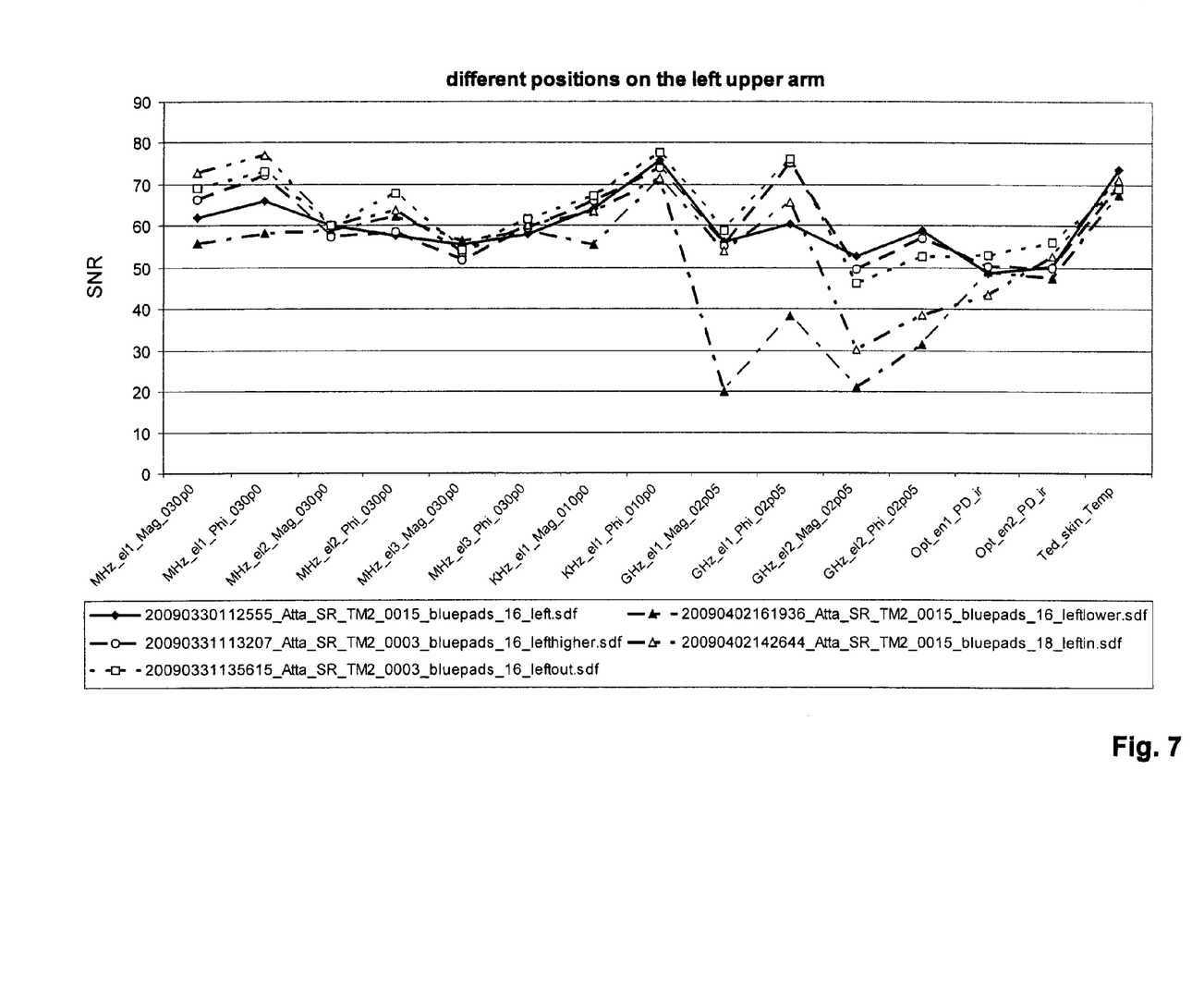
FIG. 7 shows the signal-to-noise ratios of the device at differing positions.

The device was placed at five different positions, and the SNR of the various signals was measured for all of them. The SNR dataset corresponding to correct position (antero-laterally to the upper arm, on the middle of the musculus biceps brachii, three fingers above the fossa anconal, FIG. 4) is shown in FIG. 7 with the suffix "left" in its name.

Then, the device was offset from the correct position horizontally as well was vertically and the SNR of the various signals was measured. The SNR data sets in FIG. 7 are as follows:

suffix "lefthigher": Offset from the correct position upwards by 1-4 cm, on an average about 2 cm.

suffix "leftlower": Offset from the correct position downwards by 1-4 cm, on an average about 2 cm.

suffix "leftin": Offset from the correct position horizontally towards user's chest by 1-4 cm, on an average about 2 cm suffix "leftout": Offset from the correct position horizontally away from user's chest by 1-4 cm, on an average about 2 cm As can be seen, the correctly positioned device shows good, consistent SNR values for all signals, while the other devices exhibit poorer SNR values for at least some of the signals.

b) Band Length

Figure 8:
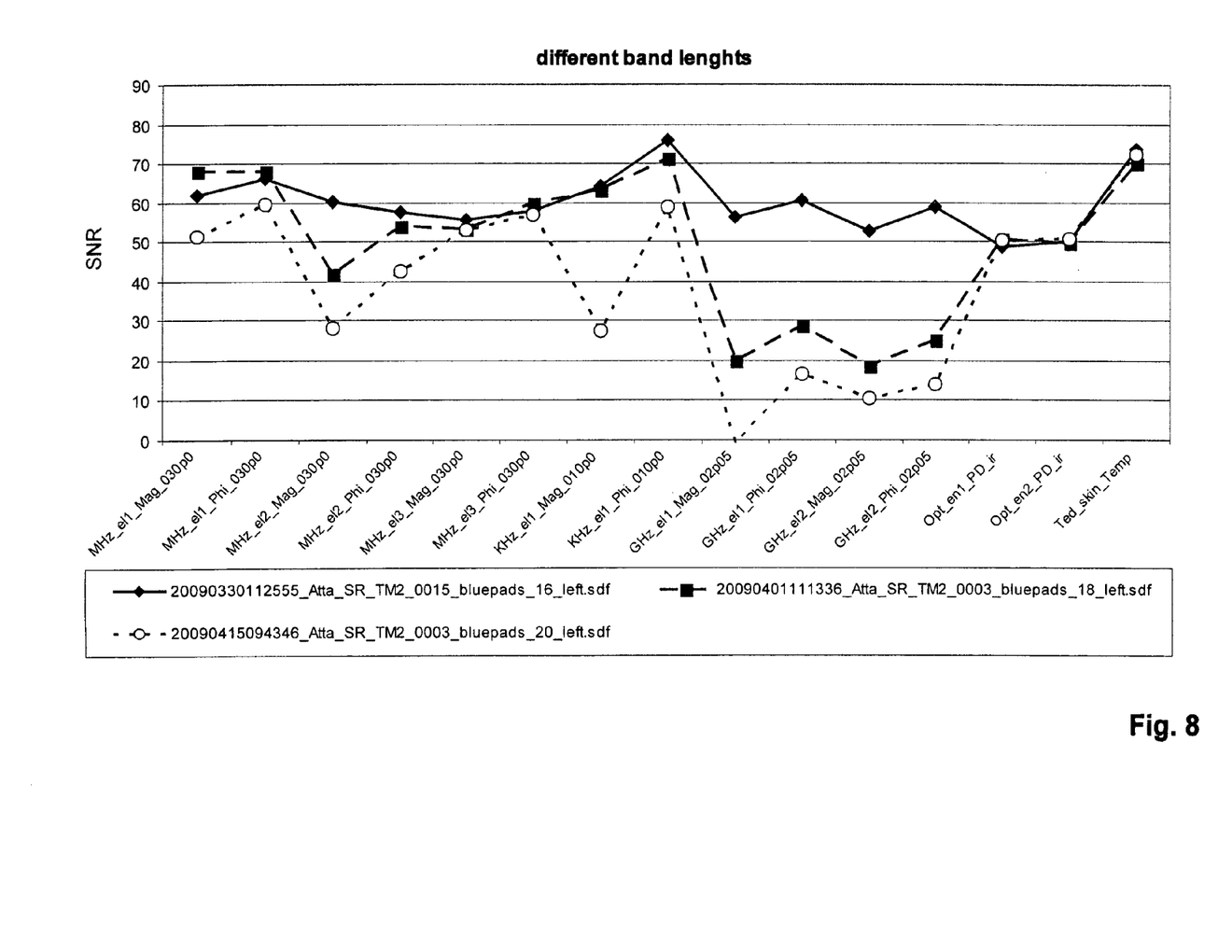
FIG. 8 shows the signal-to-noise ratios for devices with differing band lengths.

In a further set experiments, the effect of band length (and tension) on the SNR was measured. For this purpose, the SNR was determined for the same device using bands of three different lengths. The corresponding results are shown in FIG. 8. The length of the band was 16, 18 and 20 cm, respectively, corresponding to the datasets having "_16_", "_18_" and "_20_" in their names.

As can be seen, the shortest band leads to the best SNR values, while longer bands show poorer performance.

c) Strips

For assessing the influence of the strips 10 on the signal quality, the SNR values were measured for a device with strips (FIG. 9) as well as for a device without strips (FIG. 7), for each of them as a function of position (as described for FIG. 7 above). The graph of FIG. 9 shows the results for measurements of two different test runs.

Figure 9:
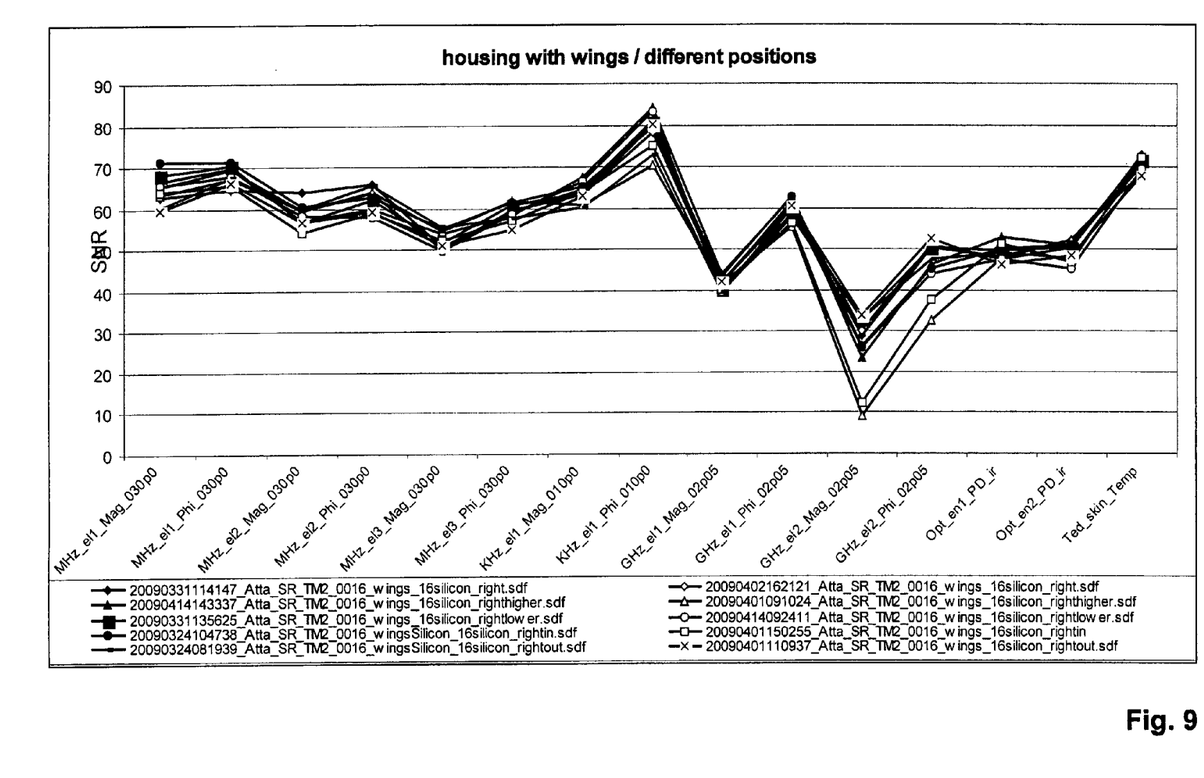
FIG. 9 shows the signal-to-noise ratios of the device at differing positions for a housing provided with flexible strips.

A comparison between the two graphs show that the variation between the various curves in FIG. 7 is larger than the variation between the various curves in FIG. 9. In other words, a device with strips shows more consistent results with smaller dependence on the placing of the device, thus making the device less sensitive to mispositionings.

While there are shown and described presently preferred embodiments of the invention, it is to be distinctly understood that the invention is not limited thereto but may be otherwise variously embodied and practiced within the scope of the following claims.

The invention claimed is:

1. A wearable sensor device for measuring a physiological parameter of a wearer, said device comprising
   a housing comprising at least one sensor arranged on a first side of said housing to be applied against the wearer's skin,
   a flexible band connected to said housing for being wound around a body part of the wearer and for holding the first side of said housing against the wearer's skin, wherein said band has a first side to be facing said wearer's skin,
   at least one stopper device arranged over a surface of the first side of said housing or of said band, wherein said stopper device has a higher coefficient of static friction than said surface
   wherein said stopper device comprises a flexible strip having a first end attached to said housing and extending along part of the first side of said band, wherein a second end of said strip opposite said first end is movable with respect to said band, and
   wherein said strip has a higher coefficient of static friction with respect to said skin than with respect to the first surface of said band.

2. The sensor device of claim 1, further comprising a strap attached to said strip and extending around said band for holding said strip against said band.

3. The sensor device of claim 1, comprising a first strip and a second strip arranged at opposite sides of said housing, with said first strip located at a first end of said band and said second strip located at a second end of said band.

4. The sensor device of claim 1, wherein said strip has a width approximately equal to a width of said band.

5. A wearable sensor device for measuring a physiological parameter of a wearer, said device comprising
   a housing comprising at least one sensor arranged on a first side of said housing to be applied against the wearer's skin,
   a flexible band connected to said housing for being wound around a body part of the wearer and for holding the first side of said housing against the wearer's skin, wherein said band has a first side to be facing said wearer's skin,
   at least one stopper device arranged over a surface of the first side of said housing or of said band, wherein said stopper device has a higher coefficient of static friction than said surface, and
   at least one stopper device affixed to the first side of said housing.

6. The sensor device of claim 5, comprising at least a first and a second stopper device at opposite sides of said sensor.

7. The sensor device of 5, wherein said stopper device is longitudinal with a longitudinal axis extending transversally with respect to a longitudinal axis of said band.

8. The sensor device of claim 5, wherein said housing forms a recess, wherein said sensor is arranged at a bottom of said recess and said stopper device is arranged on at least one side wall of said recess, with said side wall being inclined with respect to said bottom, and in particular wherein said bottom is substantially flat once filled with the sensor.

9. The sensor device of claim 1, comprising at least one stopper device affixed to the first side of said band.

10. The sensor device of claim 1, comprising at least one array of nubs affixed to the first side of said band.

11. The sensor device of claim 1, wherein said band is elastically distendable along a longitudinal direction thereof with an elasticity being in a range of 0.20 to 0.32 N/%, in particular 0.26 N/%, with said elasticity expressing a change of force at 1% change of length.

12. The sensor device of claim 1, wherein at least a surface of said stopper device is of silicone.

13. The sensor device of claim 1, wherein said band is moisture permeable and wherein the first side of said band is of a hydrophobic material and a second side of said band, which is opposite to said first side, is of a hydrophilic material.

* * * * *